United States Patent [19]
Saito et al.

[11] Patent Number: 6,025,312
[45] Date of Patent: *Feb. 15, 2000

[54] ANTIBACTERIAL, BACTERICIDAL AND ANTISEPTIC AGENT, DERMATOLOGIC PREPARATION AND DETERGENT COMPOSITION

[75] Inventors: Yoshinobu Saito, Habikino; Nobuyuki Kishi, Ibaragi; Katsuhito Kita, Takatsuki; Natsue Hirano, Ibaragi; Tetsuo Nishina, Takatsuki, all of Japan

[73] Assignee: P & PF Co., Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/894,020
[22] PCT Filed: Apr. 1, 1996
[86] PCT No.: PCT/JP96/00920
  § 371 Date: Jul. 23, 1997
  § 102(e) Date: Jul. 23, 1997
[87] PCT Pub. No.: WO97/02025
  PCT Pub. Date: Jan. 23, 1997

[30] Foreign Application Priority Data

Jun. 30, 1995 [JP] Japan .................................. 7-188545
Dec. 4, 1995 [JP] Japan .................................. 7-344461

[51] Int. Cl.$^7$ .................................................. A61K 31/12
[52] U.S. Cl. ........................ 510/130; 510/131; 510/134; 510/199; 510/505; 510/382; 510/383
[58] Field of Search ..................... 510/131, 134, 510/199, 505, 130, 382, 383

[56] References Cited

U.S. PATENT DOCUMENTS

| | | | |
|---|---|---|---|
| 5,527,492 | 6/1996 | Hayakawa | 252/546 |
| 5,658,584 | 8/1997 | Yamaguchi | 424/405 |
| 5,696,169 | 12/1997 | Otsu et al. | 514/675 |
| 5,700,449 | 12/1997 | Katayama et al. | 424/49 |

FOREIGN PATENT DOCUMENTS

| | | |
|---|---|---|
| 835655 | 4/1998 | European Pat. Off. . |
| 6-279271 | 10/1994 | Japan . |
| 7-69873 | 3/1995 | Japan . |
| 95 113057 | 5/1995 | Japan . |
| WO 97/02025 | 1/1997 | WIPO . |

*Primary Examiner*—Kery Fries
*Attorney, Agent, or Firm*—Birch, Stewart, Kolasch & Birch, LLP

[57] ABSTRACT

This invention is an antibacterial, bactericidal and antiseptic agent containing an aluminum salt of hinokitiol or/and a complex compound of hinokitiol with an aluminum compound as an effective component.

As hinokitiol contained in the form of an aluminum salt of hinokitiol or/and a complex compound of hinokitiol with an aluminum compound, the thermal, optical and chemical instabilities of hinokitiol are dispelled, and the stabilization during the production and at the time of storage as preparations is obtained.

8 Claims, No Drawings

ANTIBACTERIAL, BACTERICIDAL AND ANTISEPTIC AGENT, DERMATOLOGIC PREPARATION AND DETERGENT COMPOSITION

FIELD OF TECHNOLOGY

The present invention relates to an antibacterial, bactericidal and antiseptic agent exhibiting superior antibacterial and bactericidal actions and superior antiseptic action on a compounded agent, and having safety against a human body and storage stability for long term, and a dermatologic preparation and a detergent composition containing the antibacterial, bactericidal and antiseptic agent as an effective component.

BACKGROUND OF TECHNOLOGY

Hinokitiol (4-isopropyl-2-hydroxy-cyclohepta-2,4,6-triene-1-on) is a substance which is obtained as a product extracted from natural products such as a hinoki oil, a hiba oil and the like or by chemical synthesis. It is already known that this hinokitiol has a property that it is superior in antibacterial, bactericidal and antiseptic effects, and further low stimulative for skin of the human body and the like, as disclosed in International Patent Publication (Unexamined) WO No.92-05240, Japanese Patent Publication (Unexamined) Hei No.5-21436 and the like.

As hinokitiol has such properties., it has been compounded in cosmetics for dermatologic preparation such as a lotion, an latex, a cream, a pack and the like (Japanese Patent Publication (Unexamined) Hei No.1-199908, Japanese Patent Publication (Unexamined) Hei No.2-694119), further compounded as an effective component in a dermatologic detergent (Japanese Patent Publication (Unexamined) Hei No.3-63216), and compounded in the preventives and remedies of parodontopathy (Japanese Patent Publication (Unexamined) Show No.63-188619).

However, hinokitiol in nature is optically, thermally and further chemically unstable in the extreme, and even if hinokitiol is contained as an ingredient in a dermatologic preparation, a detergent composition and the like, the characteristics of hinokitiol are quite same.

Further, when hinokitiol contained in a compounded agent is decomposed, its antibacterial and the like activities are not only extinguished, but also, for example, the cleansing property of the compounded agent itself and the like deteriorate or are discolored, and further hinokitiol has defects that as it adheres on the wall of a container of the compounded agent owing to its low sublimation point (about 5° C.), the wall of a container is discolored and the like. Therefore, various compositions for stabilizing hinokitiol have been studied.

As conventional compositions, there are a composition for mouth compounding a compound containing a sterin nucleus such as cholesterin or the like disclosed in Japanese Patent Publication (Unexamined) Show No.63-188619, and a composition as antibacterial and funginert cosmetics compounding a zinc compound disclosed in International Patent Publication (Unexamined) WO93-17559.

However, although any one of these compositions showed dermatologic absorbability and antibacterial effect at the passage of from 6 to 24 hours after compounding hinokitiol for preparation, successive characteristics such as storage stability and the like are not illustrated at all, and the direct content of the successive stability of a compounded agent of hinokitiol is not contained at all.

Therefore, the purpose of the present invention is to provide an antibacterial, bactericidal and antiseptic agent capable of optically, thermally and chemically stabilizing hinokitiol in succession and at the same time continuously and effectively exhibiting its natural antibacterial and the like effects, and a dermatologic preparation and a composition for a detergent composition capable of stably containing and keeping hinokitiol for long term.

DISCLOSURE OF THE INVENTION

The present invention is first of all, an antibacterial, bactericidal and antiseptic agent is characterized in comprising an aluminum salt of hinokitiol or/and a complex compound of hinokitiol with an aluminum compound.

The antibacterial, bactericidal and antiseptic agent of the present invention can be produced as a liquid agent, for example, by a method of preparing a mixed solution of hinokitiol or its salt with ethanol, water and the like, and adding and mixing the mixed solution in a aqueous solution of the aluminum compound or non aqueous solution of a liquid paraffin and the like, or a mixed solution thereof. Further, the liquid agent obtained can be processed as a powder agent through respective processes of further concentrating, solidifying by drying and pulverizing.

Further, as hinokitiol, a hinoki oil, a hiba oil and the like of its starting material can be used as they are. Further, the above-mentioned salt of hinokitiol includes a salt with alkali metals such as sodium, potassium, lithium and the like, a salt with alkali earth metals such as magnesium, calcium and the like, a salt with inorganic metals such as copper, manganese and the like, a salt with diethanolamine, triethanolamine and the like, a salt with hetero cyclic amines such as morpholine, piperazine and the like, and a salt with basic amino acids such as arginine, lysine, hystidine and the like.

Further, as the non aqueous solvent, a liquid paraffin, toluene, glycerol and the like can be used.

Further, emulsifying agents such as sucrose fatty acid ester, a custor oil hardened with a polyoxyethylene and the like can be added and prepared as a latex.

According to the above-mentioned latter production method, the aluminum salt of hinokitiol or/and the complex compound of hinokitiol with an aluminum compound are formed in the antibacterial, bactericidal and antiseptic agent by chemical reaction in the process of production. Therefore, in this case, hinokitiol comes to be contained in a state of the salt with aluminum, the complex compound with an aluminum compound or a mixture thereof in the antibacterial, bactericidal and antiseptic agent, depending on the kind of the aluminum compound compounded, a state such as a PH value of the solution or the like. Further, as the above-mentioned aluminum compound forming the complex compound with hinokitiol, aluminum oxide, aluminum hydroxide and its salt or a complex compound, aluminic acid and its salt or a complex compound, complex compounds such as chlorohydroxy aluminum and the like, a salt with inorganic acidic compounds such as aluminum chloride, aluminum fluoride, aluminum sulfate, aluminum nitrate, aluminum borate, aluminum phosphate, potassium alum, ammonium alum, sodium alum, acid clay, zeolite and the like and its complex compound, and an aluminum salt of the following organic acidic compound can be used.

As the organic acidic compound, aluminum salts of a mono basic or dibasic carboxylic acid such as aluminum acetate, aluminum propionate, aluminum tartarate, aluminum lactate, aluminum citrate, aluminum gluconate, aluminum salicylate, aluminum benzoate and the like, aluminum salts of a fatty acid such as aluminum laurate, aluminum myristate, aluminum palmitate, aluminum stearate, aluminum isostearate, aluminum oleate and the like, aluminum salts of a amino acid such as aluminum glutamate, aluminum aspartate, aluminum sarcosinate, aluminum β-alanate and the like, aluminum salts of an anionic surface active agent such as aluminum acylglutamate, aluminum salt of acylmethyl tauline, aluminum salt of acyl-β-methylalanine, aluminum polyoxyethylenealkyl ether carboxylate, aluminum sulfosuccinate, aluminum polyoxyethylene sulfosuccinate, aluminum phosphate, aluminum alkylsulfate and the like, a substitution product with aluminum of organic polymer compounds such as alginic acid, chondroitin sulfate, fumic acid, hyaluronic acid, glycyrrhizic acid, polyacrylic acid, dextran sulfate and the like, etc. can be mentioned.

According to the antibacterial, bactericidal and antiseptic agent of such composition, antibacterial and the like actions effective for gram negative fungi such as Escherichia, *Pseudomonas aeruginosa* and the like, and gram positive fungi such as *Staphylococcus aureus*, methicillin resistant *Staphylococcus aureus* and the like are exhibited and the actions keep the storage stability for long term.

In the antibacterial, bactericidal and antiseptic agent relating to the present invention, the complex compound of hinokitiol with the aluminum compound particularly consists of the aluminum compound at a molar ratio of 5 mole or more per 100 mole of hinokitiol. When the amount mixed of the aluminum compound is less than 5 mole, hinokitiol is not stabilized, and it causes the deterioration of the antibacterial property and the like. Further, the upper limit of the amount mixed of the aluminum compound is not particularly restricted, and it can be mixed in excess unless the usability of said preparation and the like are not damaged.

Then, the dermatologic preparation relating to the present invention is characterized in comprising the above-mentioned antibacterial, bactericidal and antiseptic agent as an effective component. Therefore, the dermatologic preparation includes one which contains the aluminum salt of hinokitiol or/and the complex compound of hinokitiol with an aluminum compound or both of them as an effective component in the same manner as in the above-mentioned antibacterial, bactericidal and antiseptic agent.

The aluminum salt of hinokitiol and the like in the dermatologic preparation may be contained by a method of preliminarily preparing hinokitiol as its salt or the complex compound and mixing this in other essential component of said dermatologic preparation, but maybe well by a method of obtaining it as its salt or the complex compound in a reaction system during the production process of said dermatologic preparation. In the dermatologic preparation, the antibacterial property and the like of hinokitiol contained are successively stabilized even in the essential component of the dermatologic preparation owing to the reaction with an aluminum ion or the aluminum compound constituting its salt or the complex compound, and act so as to multiplically improve the properties.

Further, the content of the aluminum salt of hinokitiol or the complex compound with an aluminum compound colors the obtained dermatologic preparation in white-type color tone, and further does not generate an odor derived from an original hinokitiol. It is considered that the action of preventing the occurrence of the odor is derived from the decrease of vapor pressure of hinokitiol in the presence of an aluminum ion or the aluminum compound.

Further, it is possible to mix at a molar ratio of 5 mole or more of the aluminum compound per 100 mole of hinokitiol in the preparation of the complex compound of hinokitiol with the aluminum compound. Further, when the amount mixed of the aluminum compound is less than 5 mole, the stabilization of hinokitiol is insufficient, and it causes the deterioration of the antibacterial property and the like. Further, the upper limit of the amount mixed of the aluminum compound is not particularly restricted, and an excessive amount more than the equivalent of the above-mentioned complex compound can be mixed unless the properties such as the usability and the like of said dermatologic preparation are not damaged.

In addition to a dermatologic sterilizer prepared in the form in which the above-mentioned antibacterial, bactericidal and antiseptic agent is just impregnated to nonwoven fabrics, the dermatologic preparation of the present invention includes various kind of preparations capable of dermatologically using such as a cream, a latex, a lotion, an oil agent, a cosmetic water, a pack agent, a bathing agent, a sterilizer for athlete's foot, a hair growth promoter, an antiperspirant and the like. Accordingly, an essential basic ingredient corresponding to a kind of the preparation is contained in the dermatologic preparation. The essential basic ingredient includes a glycerin fatty acid ester, a sucrose fatty acid ester, hydrocarbons such as vaseline, paraffin and the like, glycerin, a phosphatide, a fatty acid, a higher alcohol, a multivalent alcohol, a silicon, oils and fats, gelating agents such as a carboxyvinyl polymer, a carboxymethyl cellulose and the like, a nylon powder and a polyethylene powder, deionized water, ethinylestradiol, dipotassium glycyrrhizate, Japanese green gentian extract liquid, aluminum chlorohydrate and the like.

Further, other arbitrary ingredients can be suitably compounded within a range that the action and effect of the present invention are not damaged. As the arbitrary ingredients, animal or vegetable extracts such as a collagen, a hydrolyzed collagen, a cholesterol, α-orizanol, Rice bran extract, *Matricaria chamomilla* extract, an aloe, a scutellaria root, a beefsteak plant, an artemisia princeps, a ginkgo biloba and the like, vitamins such as vitamin A, vitamin A palmitate, vitamin E, vitamin E acetate, vitamin C, vitamin C ester and the like, amino acids such as L-proline, L-glutamine, L-algin, hyaluronic acid, chondroitin sulfate and these salt, humectants such as lactic acid, sodium lactate, lactic acid ester and the like, crude drugs such as day lily, *Rehmannia glutinosa, Coptis japonica*, a lithospermum root, a carrot, surface active agents such as a POE hardening castor oil, a POE-POP block polymer, a POE sorbitan ester and the like, propylene glycol, ethylenediamine tetraacetic acid, ethanol, lauryldimethyamine oxide, a silicon-treated talc, silicic anhydride, trichlosan, dimethylpolysiloxane, other perfume and the like are mentioned.

The aluminum salt of hinokitiol, the complex compound of hinokitiol with an aluminum compound or both of them can be compounded in an amount of from 0.01 to 5% by weight based on the total amount of said dermatologic preparation in the dermatologic preparation. When the compounding amount of the salt and the like is less than 0.01% by weight, the antibacterial, bactericidal and antiseptic properties of the dermatologic preparation become insufficient. When the compounding amount exceeds 5.0% by weight, it becomes an excessive amount for the antibacterial and the like properties, and for example, in case of a cream agent, there occurs an evil that its spread and gloss deteriorate, physical properties are damaged, and it causes the deterioration of usability and the like, etc. Further, the compounding amount of the salt and the like is preferably from 0.05 to 2.0% by weight from the viewpoint of stabilizing and exhibiting the antibacterial and the like properties without causing such evil.

Then, the detergent composition relating to the present invention is characterized in comprising the above-mentioned antibacterial, bactericidal and antiseptic agent as an effective component. Therefore, the detergent composition includes one containing the aluminum salt of hinokitiol or the complex compound of hinokitiol with an aluminum compound or both of them as an effective component in the same manner as in the above-mentioned antibacterial, bactericidal and antiseptic agent.

Further, it is similar as in the case of the dermatologic preparation that the aluminum salt of hinokitiol and the like in the detergent composition can be contained by a method of preliminarily preparing hinokitiol as its salt or a complex compound and mixing this in other essential component of said detergent composition, or a method of obtaining it as its salt or a complex compound in a reaction system during the production process of said detergent composition.

Further, in the detergent composition, the antibacterial property and the like of hinokitiol contained are successively stabilized even in the essential component of the detergent composition owing to the reaction with an aluminum ion or the aluminum compound constituting its salt or the complex compound, and act so as to multiplically improve the properties. Further, an odor derived from an original hinokitiol is suppressed in the presence of an aluminum ion or an aluminum compound.

In the detergent composition, the total amount of the aluminum salt of hinokitiol, the complex compound of hinokitiol with an aluminum compound or both of them can be compounded as the amount of hinokitiol in an amount of from 0.001 to 10% by weight based on the total amount of said detergent composition, and preferably from 0.01 to 1% by weight. When the compounding amount of the salt and the like is less than 0.001% by weight, the antibacterial, bactericidal and antiseptic effects of the detergent composition become insufficient. Further, when the compounding amount exceeds more than 10% by weight, the component of hinokitiol having non aqueous property is separated from other detergent components to cause the deterioration of its cleansing property, and an odor inherent in hinokitiol is excessively generated. Therefore, the compounding amount is preferably from 0.01 to 1% by weight from the view point of obtaining the antibacterial and the like properties without causing such evil, and superior in a point being able to economically produce.

A dermatologic detergent, a rinse, a cleanser for shampoo, a detergent for food, a detergent for a table ware, a detergent for instruments, and further detergents for mouth such as a dentifrice and the like are included in the detergent composition of the present invention.

Further, these properties are liquid, jelly, creamy, and solid, and a transparent one and an opaque one are also included. Accordingly, the basic detergent component is compounded in the detergent composition in accordance with its kind.

The basic detergent ingredient includes oils and fats or mixed oils and fats thereof such as a coconut oil, a palm nucleus oil, a beef tallow and the like, an alkali metal salt of fatty acids or mixed fatty acids thereof such as a coconut oil fatty acid, lauric acid, myristic acid, stearic acid, isostearic acid and the like, an organic amine and a salt of a basic amino acid or the mixed salt thereof, anionic surface active agents such as an acidic N-acylamino acid salt, a neutral N-acylamino acid salt, a polyoxyethylenealkyl sulfuric acid ester salt, N-acyl-N-methyltaurine salt, a phosphoric acid ester salt, a sulfosuccinic acid salt, α-olefin sulfonic acid salt, a polyoxyethylene ether carboxylic acid salt and the like, nonionic surface active agents such as a POE POP block polymer, an alkanolamide, a polyoxyethylenealkyl ether and the like, amphoteric surface active agents such as an imidazorium betaine, an amidoacetic acid betaine and the like, a sucrose fatty acid ester, a silicic anhydride saccharin sodium, sodium laurylsulfate and the like.

Further, other arbitrary components can be suitably compounded within a range that the action and effect of the present invention are not damaged.

As the arbitrary components, humectants such as glycerol, diglyceride, sorbitol, a hyaluronic acid salt, a chondroitin salt and the like, a higher alcohol, oils such as a hohoba oil, a rice embryo oil, an olive oil and the like, gelating agents such as carboxymethyl cellulose and the like, a thickening agent, a xanthane gum, a perfume, a pigment, a chelate agent, an ultraviolet rays absorbent, an antioxidant, animal or vegetable extract liquids such as a crude drug and the like, usability-improving agents such as a cationic polymer, a lactate and the like.

Further, it is possible to mix at a molar ratio of 5 mole or more of the aluminum compound per 100 mole of hinokitiol in the preparation of the complex compound of hinokitiol with the aluminum compound. W hen the amount mixed of the aluminum compound is less than 5 mole, the stabilization of the antibacterial and the like properties of hinokitiol is insufficient. Further, when the amount mixed of the aluminum compound is less than 30 mole, the detergent may be colored in brown to yellow, depending on the base material of said detergent composition, and when it exceeds 400 mole, the transparent base material may be opaque. Therefore, the amount mixed is preferably from 30 to 400 mole.

EXAMPLE

Example 1

Example of the antibacterial, bactericidal and antiseptic agent was obtained by a method of simply mixing the respective compounding components shown in a sample No. 1 of the following Table 1 under normal temperature (20° C.)

TABLE 1

|  | Sample No. | | | |
| --- | --- | --- | --- | --- |
|  | Example | Comparative Example | | |
| Compounding component | 1 | 2 | 3 | 4 |
| Hinokitiol | 5 | 5 | — | — |
| Aluminum distearate | 18.6 | — | — | 18.6 |
| 95% official alcohol | 60 | 60 | 60 | 60 |
| Distilled water | 16.4 | 35 | 40 | 21.4 |

(Value unit in Table: weight %)

Further, samples No. 2 to 4 were Comparative Examples, and obtained by the same method as described above.

The above-mentioned respective samples were diluted with sterilized water according to the relationship shown in the following Table 2.

TABLE 2

| Diluted sample No. | Sample No. | Amount of sample (ml) | Amount of diluted liquid (ml) | Concentration of hinokitiol (ppm) |
|---|---|---|---|---|
| 1-1 | 1 | 0.01 | 10 | 50 |
| 2-1 | 2 | 0.01 | 10 | 50 |
| 1-2 | 1 | 0.1 | 10 | 500 |
| 2-2 | 2 | 0.1 | 10 | 500 |
| 1-3 | 1 | 0.2 | 10 | 1000 |
| 2-3 | 2 | 0.2 | 10 | 1000 |
| 3-1 | 3 | 0.2 | 10 | — |
| 4-1 | 4 | 0.2 | 10 | — |

The following test of bactericidal effect for respective samples described above was carried out.

(1) Method of the test of bactericidal effect

① 5 ml of respective diluted samples No. 1-1 to 4-1 diluted as Table 2 were respectively injected in sterilized tubes and stirred with vortex.

② Further, the microbe to be tested was obtained by preparing a fresh microbe subcultured on the previous day at McFarland 0.5($10^6$ CFU/ml) in sterilized physiological salt solution, mixing with a platinum rod and incubating for a fixed time.

③ Then, 50 μl of the microbe solution of ② was inoculated on the sample of ①, the 50 μl was inoculated on Trypt-soy agar medium (BBL) to which 5% sheep blood was added.

④ Then, the above-mentioned inoculation medium was stirred with glass beads, cultured under a condition of a constant temperature of 35° C. for night and day, and the number of colonies grown was counted.

⑤ Further, the microbes tested were *Pseudomonas aeruginosa* (*P. aeruginosa*), methicillin resistant Staphylococcus aureus (MRSA), *Staphylococcus aureus* (MSSA) and Escherichia (*E. coli*).

(2) The results of this test were shown in the following Tables 3 to 5.

Further, the test results of the diluted samples No. 3-1 and No. 4-1 were shown as Comparative Examples in the following Table 6.

TABLE 3

| Diluted sample No. | 1-1 | | | | | 2-1 | | | | |
|---|---|---|---|---|---|---|---|---|---|---|
| Kind of microbe\action time | 5 min. | 15 min. | 30 min. | 60 min. | 120 min. | 5 min. | 15 min. | 30 min. | 60 min. | 120 min. |
| *P. aeruginosa* 1 | $10^3$ | $10^2$ | 20 | 4 | (—) | $10^3$ | $10^3$ | $10^3$ | $10^3$ | $10^2$ |
| *P. aeruginosa* 2 | $10^2$ | 53 | 7 | (—) | 2 | $10^3$ | $10^3$ | $10^3$ | $10^3$ | $10^2$ |
| *P. aeruginosa* 3 | $10^2$ | 39 | (—) | (—) | (—) | $10^3$ | $10^3$ | $10^3$ | $10^3$ | $10^3$ |
| MRSA 9457 | $10^3$ | $10^2$ | 28 | 2 | (—) | $10^3$ | $10^3$ | $10^3$ | $10^3$ | $10^3$ |
| MRSA 9458-1 | $10^2$ | 48 | 3 | (—) | (—) | $10^3$ | $10^3$ | $10^3$ | $10^3$ | $10^3$ |
| MRSA 9457-2 | $10^2$ | 21 | 2 | (—) | (—) | $10^3$ | $10^3$ | $10^3$ | $10^3$ | $10^2$ |
| MRSA 9462-1 | $10^3$ | $10^2$ | 14 | (—) | (—) | $10^3$ | $10^3$ | $10^3$ | $10^3$ | $10^2$ |
| MRSA 84-9638 | $10^2$ | 67 | 19 | 1 | (—) | $10^3$ | $10^3$ | $10^3$ | $10^3$ | $10^2$ |
| MRSA 9455-2 | $10^3$ | $10^2$ | 11 | (—) | (—) | $10^3$ | $10^3$ | $10^3$ | $10^3$ | $10^2$ |
| MSSA 9463 | $10^2$ | 62 | (—) | (—) | 3 | $10^3$ | $10^3$ | $10^3$ | $10^3$ | $10^2$ |
| MSSA 84-9644 | $10^2$ | 44 | (—) | (—) | (—) | $10^3$ | $10^3$ | $10^3$ | $10^3$ | $10^2$ |
| *E. coli* 1 | $10^3$ | $10^2$ | 18 | 3 | (—) | $10^3$ | $10^3$ | $10^3$ | $10^3$ | $10^2$ |
| *E. coli* 2 | $10^2$ | $49^3$ | (—) | (—) | (—) | $10^3$ | $10^3$ | $10^3$ | $10^3$ | $10^2$ |

Further, the standard of judgment is as follows.
(—): No growth of microbes is recognized.
$10^2$: More than $10^2$ CFU/ml (uncountable)
$10^3$: More than $10^3$ CFU/ml (uncountable)

TABLE 4

| Diluted sample No. | 1-2 | | | | | 2-2 | | | | |
|---|---|---|---|---|---|---|---|---|---|---|
| Kind of microbe\action time | 5 min. | 15 min. | 30 min. | 60 min. | 120 min. | 5 min. | 15 min. | 30 min. | 60 min. | 120 min. |
| *P. aeruginosa* 1 | $10^3$ | $10^2$ | 61 | 5 | (—) | $10^3$ | $10^3$ | $10^3$ | $10^3$ | $10^3$ |
| *P. aeruginosa* 2 | $10^3$ | $10^3$ | $10^2$ | 16 | 3 | $10^3$ | $10^3$ | $10^3$ | $10^3$ | $10^3$ |
| *P. aeruginosa* 3 | $10^3$ | $10^2$ | 51 | 2 | (—) | $10^3$ | $10^3$ | $10^3$ | $10^3$ | $10^3$ |
| MRSA 9457 | $10^3$ | $10^2$ | 61 | 9 | (—) | $10^3$ | $10^3$ | $10^3$ | $10^3$ | $10^3$ |
| MRSA 9458-1 | $10^3$ | $10^2$ | 47 | 11 | (—) | $10^3$ | $10^3$ | $10^3$ | $10^3$ | $10^3$ |
| MRSA 9457-2 | $10^3$ | $10^2$ | 38 | (—) | (—) | $10^3$ | $10^3$ | $10^3$ | $10^3$ | $10^3$ |
| MRSA 9462-1 | $10^3$ | $10^2$ | 77 | 21 | 2 | $10^3$ | $10^3$ | $10^3$ | $10^3$ | $10^3$ |
| MRSA 84-9638 | $10^3$ | $10^2$ | 65 | 6 | (—) | $10^3$ | $10^3$ | $10^3$ | $10^3$ | $10^3$ |
| MRSA 9455-2 | $10^3$ | $10^2$ | 58 | 13 | (—) | $10^3$ | $10^3$ | $10^3$ | $10^3$ | $10^3$ |
| MSSA 9463 | $10^3$ | $10^2$ | 39 | (—) | (—) | $10^3$ | $10^3$ | $10^3$ | $10^3$ | $10^3$ |
| MSSA 84-9644 | $10^3$ | $10^2$ | 59 | 7 | (—) | $10^3$ | $10^3$ | $10^3$ | $10^3$ | $10^3$ |
| *E. coli* 1 | $10^3$ | $10^2$ | 87 | 3 | (—) | $10^3$ | $10^3$ | $10^3$ | $10^3$ | $10^3$ |
| *E. coli* 2 | $10^3$ | $10^2$ | 41 | (—) | (—) | $10^3$ | $10^3$ | $10^3$ | $10^3$ | $10^3$ |

Further, the standard of judgment is the same as in case of Table 3.

TABLE 5

| Diluted sample No. | 1-3 | | | | | 2-3 | | | | |
| --- | --- | --- | --- | --- | --- | --- | --- | --- | --- | --- |
| Kind of microbe\ action time | 5 min. | 15 min. | 30 min. | 60 min. | 120 min. | 5 min. | 15 min. | 30 min. | 60 min. | 120 min. |
| P. aeruginosa 1 | $10^3$ | $10^3$ | $10^2$ | 11 | (—) | $10^3$ | $10^3$ | $10^3$ | $10^3$ | $10^3$ |
| P. aeruginosa 2 | $10^3$ | $10^2$ | $10^2$ | 34 | 1 | $10^3$ | $10^3$ | $10^3$ | $10^3$ | $10^3$ |
| P. aeruginosa 3 | $10^3$ | $10^2$ | $10^2$ | 7 | (—) | $10^3$ | $10^3$ | $10^3$ | $10^3$ | $10^3$ |
| MRSA 9457 | $10^3$ | $10^3$ | $10^2$ | 22 | (—) | $10^3$ | $10^3$ | $10^3$ | $10^3$ | $10^3$ |
| MRSA 9458-1 | $10^3$ | $10^2$ | $10^2$ | 26 | (—) | $10^3$ | $10^3$ | $10^3$ | $10^3$ | $10^3$ |
| MRSA 9457-2 | $10^3$ | $10^2$ | 81 | 9 | (—) | $10^3$ | $10^3$ | $10^3$ | $10^3$ | $10^3$ |
| MRSA 9462-1 | $10^3$ | $10^3$ | $10^2$ | 43 | 4 | $10^3$ | $10^3$ | $10^3$ | $10^3$ | $10^3$ |
| MRSA 84-9638 | $10^3$ | $10^2$ | $10^2$ | 17 | (—) | $10^3$ | $10^3$ | $10^3$ | $10^3$ | $10^3$ |
| MRSA 9455-2 | $10^3$ | $10^3$ | $10^2$ | 29 | (—) | $10^3$ | $10^3$ | $10^3$ | $10^3$ | $10^3$ |
| MSSA 9463 | $10^3$ | $10^3$ | 74 | 6 | (—) | $10^3$ | $10^3$ | $10^3$ | $10^3$ | $10^3$ |
| MSSA 84-9644 | $10^3$ | $10^2$ | $10^2$ | 17 | (—) | $10^3$ | $10^3$ | $10^3$ | $10^3$ | $10^3$ |
| E. coli 1 | $10^3$ | $10^2$ | 59 | 8 | (—) | $10^3$ | $10^3$ | $10^3$ | $10^3$ | $10^3$ |
| E. coli 2 | $10^3$ | $10^2$ | 45 | (—) | (—) | $10^3$ | $10^3$ | $10^3$ | $10^3$ | $10^3$ |

Further, the standard of judgement is the same as in case of Table 3.

TABLE 6

| Diluted sample No. | 3-1 | | | | | 4-1 | | | | |
| --- | --- | --- | --- | --- | --- | --- | --- | --- | --- | --- |
| Kind of microbe/ action time | 5 min. | 15 min. | 30 min. | 60 min. | 120 min. | 5 min. | 15 min. | 30 min. | 60 min. | 120 min. |
| P. aeruginosa 1 | $10^3$ | $10^3$ | $10^3$ | $10^3$ | $10^3$ | $10^3$ | $10^3$ | $10^3$ | $10^3$ | $10^3$ |
| P. aeruginosa 2 | $10^3$ | $10^3$ | $10^3$ | $10^3$ | $10^3$ | $10^3$ | $10^3$ | $10^3$ | $10^3$ | $10^3$ |
| P. aeruginosa 3 | $10^3$ | $10^3$ | $10^3$ | $10^3$ | $10^3$ | $10^3$ | $10^3$ | $10^3$ | $10^3$ | $10^3$ |
| MRSA 9457 | $10^3$ | $10^3$ | $10^3$ | $10^3$ | $10^3$ | $10^3$ | $10^3$ | $10^3$ | $10^3$ | $10^3$ |
| MRSA 9458-1 | $10^3$ | $10^3$ | $10^3$ | $10^3$ | $10^3$ | $10^3$ | $10^3$ | $10^3$ | $10^3$ | $10^3$ |
| MRSA 9457-2 | $10^3$ | $10^3$ | $10^3$ | $10^3$ | $10^3$ | $10^3$ | $10^3$ | $10^3$ | $10^3$ | $10^3$ |
| MRSA 9462-1 | $10^3$ | $10^3$ | $10^3$ | $10^3$ | $10^3$ | $10^3$ | $10^3$ | $10^3$ | $10^3$ | $10^3$ |
| MRSA 84-9638 | $10^3$ | $10^3$ | $10^3$ | $10^3$ | $10^3$ | $10^3$ | $10^3$ | $10^3$ | $10^3$ | $10^3$ |
| MRSA 9455-2 | $10^3$ | $10^3$ | $10^3$ | $10^3$ | $10^3$ | $10^3$ | $10^3$ | $10^3$ | $10^3$ | $10^3$ |
| MSSA 9463 | $10^3$ | $10^3$ | $10^3$ | $10^3$ | $10^3$ | $10^3$ | $10^3$ | $10^3$ | $10^3$ | $10^3$ |
| MSSA 84-9644 | $10^3$ | $10^3$ | $10^3$ | $10^3$ | $10^3$ | $10^3$ | $10^3$ | $10^3$ | $10^3$ | $10^3$ |
| E. coli 1 | $10^3$ | $10^3$ | $10^3$ | $10^3$ | $10^3$ | $10^3$ | $10^3$ | $10^3$ | $10^3$ | $10^3$ |
| E. coli 2 | $10^3$ | $10^3$ | $10^3$ | $10^3$ | $10^3$ | $10^3$ | $10^3$ | $10^3$ | $10^3$ | $10^3$ |

Further, the standard of judgement is the same as in case of Table 3.

It can be recognized from these test results that excellent bactericidal effect is exhibited according to the antibacterial, bactericidal and antiseptic agent relating to the present invention as compared with Comparative Examples No. 2-1, No. 2-2, No. 2-3, No. 3-1, and No. 4-1.

Example 2

An antibacterial, bactericidal and antiseptic agent was obtained by a method of simply mixing the respective compounding components shown in a sample No. 5 of the following Table 7 under normal temperature (20° C.)

TABLE 7

| Compounding component | Sample No. 5 |
| --- | --- |
| Ethanol | 80 |
| Hinokitiol | 0.2 |
| Aluminum chloride | 2.94 |
| Deionized water | 16.86 |

(Value unit in Table: weight %)

The antibacterial, bactericidal and antiseptic agent obtained was colorless and transparent, an odor inherent in original hinokitiol did not occur, and the test results of bactericidal effect as mentioned above were good. Further, 200 ml of the agent obtained was charged in a white opaque bottle made of a polypropylene, and its storage stability by a method of standing alone under a temperature of 37° C. for 30 days was good.

The antibacterial, bactericidal and antiseptic agent can be used for multipurpose as follows. It can be used for for example, a scattering to public sandboxes, a conservation agent for food, a sterilizer for beds and the like of hospitals and in the spot of barbers and beauty parlors, an antibacterial agent for an antibacterial film and the like and for kneading in various kind of antibacterial fibers, a cleansing agent for a pet and the like, a compounded agent for sterilizing clothes and for a softening and finishing agent and the like.

Example 3

A cream agent was obtained according to the compounding components of the following Table 8.

TABLE 8

| Component partition | Compounding component | Compounding amount (weight %) |
| --- | --- | --- |
| A | Hinokitiol and its salt | 0.2 |
| | Liquid paraffin 70 | 15.0 |
| B | Vaseline | 5.0 |
| | Micro crystalline wax | 3.0 |
| | Hardened oil | 2.0 |

TABLE 8-continued

| Component partition | Compounding component | Compounding amount (weight %) |
|---|---|---|
| C | Polyoxyethylene sorbitan monostearate | 2.0 |
|   | Sodium stearate | 3.0 |
| D | Glycerol | 10.0 |
|   | 1,3BG | 5.0 |
|   | Deionized water | Residue |

Further, a method of producing the cream agent is as follows.

First of all, respective components of the component partition B were mixed and homogeneously dissolved by heating at from 70° C. to 80° C. Further, respective components of the component partitions C and D were mixed and homogeneously dissolved by heating at from 70° C. to 80° C. Then, the liquid dissolving the component partitions C and D was bit by bit added in the liquid dissolving the component partition B, and the mixture was homogeneously emulsified with a homomixer. Subsequently, the emulsified solution was cooled to 50° C., and the hinokitiol or its salt of the component partition A was added and homogeneously stirred. Then, this was cooled to 30° C. to obtain respective cream agents. Further, the hinokitiol salts were shown in Table 9.

Concerning the color tone on appearence, the odor and the antibacterial action of these cream agents, its storage stability by a method of standing alone just after production and under a temperature of 37° C. for 30 days was tested, and the results were shown in Table 9. The test of the storage stability was carried out in a state in which 60 g of the cream agents obtained was charged in a resin tube composed of three-layers material of LDPE/EVAL/HDPE and this was heat-sealed.

The mixing molar ratio was shown as the value of hinokitiol to a metal constituting its salt.

Further, when the coloration of appearance was judged with eyes, it was represented that no change of the color tone was ○, a merely slight change recognized was Δ, and a remarkable change was x. Further, the odor was judged by persons of majority according to the sense of smell of respective three panelers of men and women who were 20 years old. It was represented that no original odor of hinokitiol was ○, an original odor slightly recognized was Δ, and an original odor remarkably recognized was x.

Further, the judgment of the antibacterial action was carried out according to a method based on a glove-juice method.

Namely, first of all, paneler's both hands were washed for 15 seconds with an alkaline soap for non-medical use, and successively rinsed for 60 seconds. Then, water was removed from the both hands, 1 ml of Staphylococcus aureus (FDA209P) prepared at a concentration of $10^6$/ml was respectively rubbed on the surface of the both hands. Subsequently, 1 g of the cream agent as a sample was coated on the left hand and the right hand was a blank. Then, gloves made of a vinyl resin were put on the both hands after passage of 60 minutes, and 500 ml of a sampling solution (an aqueous solution of 0.4 g/l potassium hydrogenphosphoric acid, 10.1 g/l sodium hydrogenphosphoric acid and 1.8 g/l surface active agent) for sampling a microbe growing in the gloves which was adjusted at PH of 7.0, was injected. The both hands were vibrated in this state to separate microbes which exist on the surface of the hands. The sampled solution was coated on a SCDLP agar medium, live microbes were calculated after passage of 24 hours, and the rate of dead microbes was determined by the value calculated. As a result, the rate of dead microbes of 85% or more was referred to as ○, the rate of from 50 to 85% to as Δ, and the rate of 50% or less to as x.

TABLE 9

| | | | Just after production | | | Storage stability | | |
|---|---|---|---|---|---|---|---|---|
| Sample No. | Kind | Molar ratio mixed | Color tone | Odor | Anti-bacterial action | Color tone | Odor | Anti-bacterial action |
| Example 5 | Aluminum hinokitiolate | 3/1 | White | ○ | ○ | ○ | ○ | ○ |
| Comparative Example | | | | | | | | |
| 6 | Sodium hinokitiolate | 1/1 | Light yellow | Δ | Δ | X | X | Δ |
| 7 | Potassium hinokitiolate | 1/1 | Light yellow | Δ | X | X | X | X |
| 8 | Zinc hinokitiolate | 2/1 | Light yellow | ○ | Δ | Δ | Δ | Δ |
| 9 | Copper hinokitiolate | 2/1 | Light green | ○ | ○ | X | X | ○ |
| 10 | Iron hinokitiolate | 2/1 | Light brown | ○ | ○ | X | X | ○ |
| 11 | Calcium hinokitiolate | 2/1 | White | ○ | X | ○ | Δ | X |
| 12 | Magnesium hinokitiolate | 2/1 | Light yellow | ○ | X | Δ | Δ | X |
| 13 | Hinokitiol | — | Light yellow | X | Δ | X | X | X |
| 14 | no addition | — | White | ○ | X | ○ | ○ | X |

It can be recognized from the results shown in Table 9 that the cream agent compounding the aluminum hinokitiolate does not generate a coloration inherent in the salt and an odor inherent in hinokitiol, further keeps effective the antibacterial action, and these properties are kept at the time of a retention at a high temperature without change.

Examples 4 to 7

A latex was prepared according to the compounding components shown in the following Table 10.

TABLE 10

| Component partition | Compounding component | Compounding amount (weight %) |
|---|---|---|
| E | Aluminum hinokitiolate | 0.05 to 7.0 |
|   | Cetyl alcohol | 1.5 |
| F | Vaseline | 4.0 |
|   | Squalane | 5.0 |
|   | Liquid paraffin 70 | 1.0 |
| G | Sorbitan monooleate | 2.0 |
|   | Triethanolamine stearate | 3.0 |
| H | 1,3BG | 5.0 |
|   | PEG 1500 | 3.0 |
|   | Glycerol | 5.0 |
|   | Deionized water | Residue |

The method of producing these latexes is as follows.

First of all, respective components of the component partition F were mixed and homogeneously dissolved by heating at from 70° C. to 80° C. Further, the component partitions G and H were mixed and homogeneously dissolved by heating at from 70° C. to 80° C. Then, the liquid dissolving the component partitions G and H was bit by bit added in the liquid dissolving the component partition F, and the mixture was homogeneously emulsified with a mixer. Subsequently, the emulsified solution was cooled to 50° C., and the aluminum hinokitiolate (a molar ratio of 3:1) of the component partition E was added at a fixed compounding amount and homogeneously stirred. Then, this was cooled to 30° C. to obtain respective latexes.

Concerning the color tone on appearence, the odor and the antibacterial action of these latexes, its storage stability by a method of standing alone just after production and under a temperature of 37° C. for 30 days, and further the usability of spread and gloss were tested, and the results were shown in the following Table 11. The test of the storage stability was carried out in a state in which 150 ml of the latex obtained was charged in a glass vessel and sealed up.

Further, the judgment standard of color tone, odor and antibacterial action is the same as described above.

TABLE 11

| | Sample No. | | | | | |
|---|---|---|---|---|---|---|
| | Example | | | | Comparative Example | |
| | 15 | 16 | 17 | 18 | 19 | 20 |
| Compounding amount of aluminum hinokitiolate (weight %) Just after production | 0.01 | 0.1 | 2.0 | 5.0 | 0.005 | 7.0 |
| Color tone | White | White | White | White | White | White |
| Odor | ○ | ○ | ○ | ○ | ○ | Δ |
| Antibacterial action | ○ | ○ | ○ | ○ | Δ | ○ |
| Storage stability | | | | | | |
| Color tone | ○ | ○ | ○ | ○ | ○ | Δ |
| Odor | ○ | ○ | ○ | ○ | ○ | X |
| Antibacterial action | ○ | ○ | ○ | ○ | Δ | ○ |

According to the latex in which the compounding amount of hinokitiol of the samples No. 15 to 18 corresponding to Examples 4 to 7 is composed within a range of more than 0.01% by weight and less than 5.0% by weight, it can be recognized from the results shown in Table 11 that an odor inherent in hinokitiol does not occur, and further the latex excellent in the antibacterial action and the storage stability is obtained. Further, one excellent in the usability within a range of 5.0% by weight or less was obtained.

Examples 8 to 12

A jelly cosmetic liquid for keeping humidity was prepared according to the compounding components and compounding amounts of the following Table 12.

TABLE 12

| Compounding component | Compounding amount (weight %) |
|---|---|
| Solution of aluminum hinokitiolate | 2.0 |
| Edetic acid | 0.01 |
| 1,3BG | 10.0 |
| Glycerol | 5.0 |
| Sodium hyaluronate | 0.01 |
| POP(15)oleyl alcohol ether | 1.0 |
| Carboxyvinyl polymer | 0.4 |
| Potassium hydroxide | 0.1 |
| Deionized water | Residue |

The production method of the cosmetic liquid is as follows.

First of all, a carboxyvinyl polymer was dissolved in a part of deionized water. Subsequently, edetic acid, glycerol, hyaluronic acid, a POP(15) oleylalcohol and the complex solution of hinokitiol aluminum were dispersed in this, and further neutralized with potassium hydroxide to obtain a jell. Further, the complex solution of aluminum hinokitiolate was obtained by adding and mixing hinokitiol and ammonium chloride hexa-hydrate salt at a quantitative rate shown in the following Table 13 in aqueous ethanol solution and preparing the complex compound of hinokitiol with an aluminum compound.

TABLE 13

| Compounding component | Compounding amount (molar ratio or weight %) | | | | | | |
|---|---|---|---|---|---|---|---|
| (Complex code) | a | b | c | d | e | f | g |
| Hinokitiol/Aluminum chloride hexa-hydrate salt (molar ratio) | 100/5 | 100/20 | 100/50 | 100/100 | 100/200 | 100/3 | 100/1 |

TABLE 13-continued

| Compounding component | Compounding amount (molar ratio or weight %) | | | | | | |
|---|---|---|---|---|---|---|---|
| (Complex code) | a | b | c | d | e | f | g |
| Hinokitiol | 5 | 5 | 5 | 5 | 5 | 5 | 5 |
| Ethanol | 60 | 60 | 60 | 60 | 60 | 60 | 60 |
| Aluminum chloride hexa-hydrate salt | 0.370 | 1.481 | 3.705 | 7.406 | 14.81 | 0.222 | 0.074 |
| Deionized water | Residue | Residue | Residue | Residue | Residue | Residue | Residue |

TABLE 14

| | Sample No. | | | | | | |
|---|---|---|---|---|---|---|---|
| | Example | | | | | Comparative Example | |
| Complex code | 21 a | 22 b | 23 c | 24 d | 25 e | 26 f | 27 g |
| Just after production | | | | | | | |
| Color tone | Slightly yellow | Slightly yellow | None | None | None | Light yellow | Light yellow |
| Odor | ○ | ○ | ○ | ○ | ○ | Δ | Δ |
| Antibacterial action | ○ | ○ | ○ | ○ | ○ | Δ | Δ |
| Storage stability | | | | | | | |
| Color tone | ○ | ○ | ○ | ○ | ○ | Δ | Δ |
| Odor | ○ | ○ | ○ | ○ | ○ | Δ | Δ |
| Antibacterial action | ○ | ○ | ○ | ○ | ○ | Δ | X |

The color tone, odor and antibacterial action, and furthermore storage stability of these jells were tested and the results were shown in the following Table 14. The test of storage stability was carried out in a state in which 30 ml of the jells obtained in a glass vessel was charged and sealed up.

Further, the judgment standard of color tone, odor and antibacterial action is the same as described above.

When the compounding rate of hinokitiol of the samples No. 21 to 25 corresponding to Examples 8 to 12 to ammonium chloride hexa-hydrate salt is more than a molar ratio of 100/5, it is recognized from the results shown in Table 14 that the respective characteristics and storage stability are effective.

Examples 13 to 17

Concerning a cream obtained according to the compounding components and compounding amounts shown in the following Table 15 and obtained by compounding the complex compound of hinokitiol with aluminum tristearate which is obtained at the molar ratio shown in the following Table 16, the same test as in the above-mentioned Examples 8 to 12 was carried out. Further, preparation method and storage method were in accordance with Example 3.

Further, the judgment standard of color tone, odor and antibacterial action is the same as described above.

TABLE 15

| Component partition | Compounding component | Compounding amount (weight %) |
|---|---|---|
| I | Hinokitiol | 0.05 |
| | Aluminum tristearate | 0.0026 to 0.78 |
| J | Hydrogenated lanolin | 2.0 |
| | Squalane | 4.0 |
| | Octyldodecanol | 10.0 |
| | Behenyl alcohol | 6.0 |
| K | Sodium stearate | 3.0 |
| L | Glycerol | 10.0 |
| | 1,3BG | 10.0 |
| | Deionized water | Residue |

TABLE 16

| | Sample No. | | | | | |
|---|---|---|---|---|---|---|
| | Example | | | | | Comparative Example |
| | 28 | 29 | 30 | 31 | 32 | 33 |
| Hinokitiol/Aluminum tristearate (molar ratio) | 100/5 | 100/50 | 100/100 | 100/200 | 100/300 | 100/1 |
| Aluminum tristearate (weight %) | 0.013 | 0.13 | 0.26 | 0.52 | 0.78 | 0.0026 |
| Just after production | | | | | | |
| Color tone | Slightly yellow | White | White | White | White | Light yellow |
| Odor | ○ | ○ | ○ | ○ | ○ | Δ |
| Antibacterial action | ○ | ○ | ○ | ○ | ○ | Δ |
| Storage stability | | | | | | |
| Color tone | ○ | ○ | ○ | ○ | ○ | ○ |
| Odor | ○ | ○ | ○ | ○ | ○ | ○ |
| Antibacterial action | ○ | ○ | ○ | ○ | ○ | Δ |

When the molar ratio of the complex compound of hinokitiol with aluminum tristearate of the samples No. 28 to 32 corresponding to Examples 13 to 17 is more than 100/5, it is recognized from the results shown in Table 16 that the respective characteristics and storage stability are effective.

Example 18

A fluid lotion was prepared by the following method according to the compounding components and compounding amounts shown in the following Table 17.

TABLE 17

| Compounding component | Compounding amount (weight %) |
| --- | --- |
| Aluminum hinokitiolate | 0.1 |
| Squalane | 8.0 |
| Vaseline | 0.1 |
| POP(20) sorbitan tetraoleate | 0.3 |
| Ethanol | 15.0 |
| Kaolin | 2.0 |
| Deionized water | Residue |

The production method of the lotion is as follows. First of all, a squalane, a vaseline and POP(20) sorbitan tetraoleate were dissolved. Subsequently, a kaolin was homogeneously dispersed in the dissolved liquid, and further an ethanol solution of aluminum hinokitiolate (a molar ratio of 3:1) was added and dissolved. Then, the dissolved liquid was filtered to obtain the lotion.

As a result of carrying out the same test as in Example 3, the color tone, odor and antibacterial action, and furthermore storage stability of the lotion were good. Further, the test of storage stability was carried out by charging the lotion obtained in a 150 ml glass vessel and sealing up.

Example 19

A pack agent was prepared by the following method according to the compounding components and compounding amounts shown in the following Table 18.

TABLE 18

| Compounding component | Compounding amount (weight %) |
| --- | --- |
| Aluminum hinokitiolate | 0.05 |
| Poly(vinyl alcohol) | 13.0 |
| Carboxymethyl cellulose | 5.0 |
| 1,3BG | 5.0 |
| Ethanol | 12.0 |
| Glycerol | 3.0 |
| Diglyceride | 1.0 |
| POP(10) oleyl alcohol ether | 0.5 |
| Deionized water | Residue |

First of all, glycerol, 1,3BG and diglyceride were dissolved by heating at 70° C. Subsequently, poly(vinyl alcohol) and carboxymethyl cellulose swollen in ethanol were added to this and homogeneously dissolved.

Then, POP(10) oleyl alcohol ether and hinokitiol aluminum (a molar ratio of 3:1) were added to this and dissolved, and the mixture was cooled to 30° C. with a heat exchanger to obtain the pack agent.

As a result of carrying out the same test as in Example 3, the color tone, odor and antibacterial action, and furthermore storage stability of the pack agent were good. Further, the test of storage stability was carried out by charging the pack agent obtained in a 50 g PE tube.

Example 20

A creamy content articles and an inner film for charging the content articles were prepared by the following method according to the compound components and compound amounts of the component partition M shown in the following Table 19, and these were constituted as a capsule agent.

TABLE 19

| Component partition | Compounding component | Compounding amount (weight %) |
| --- | --- | --- |
| M | Aluminum hinokitiolate | 0.5 |
| | Liquid paraffin | 69.5 |
| | Squalane | 10.0 |
| | Vaseline | 5.0 |
| | Sorbitan oleate | 5.0 |
| | POP(10)oleyl ether | 10.0 |
| N | Gelatin | 40.0 |
| | Glycerol | 20.0 |
| | Deionized water | 40.0 |

The method of producing the capsule agent is as follows. First of all, respective components of the component partition M were prepared as dissolved solutions.

Further, aluminum hinokitiolate is a molar ratio of 3:1. And respective components of the component partition N were mixed and dissolved, and a sheet of a thickness of approximately 1 mm was formed from the solution by using a roller. This was stored in a cylindrical molding machine of a rotary type full-automatic soft-capsule molding machine, and a soft capsule film of a diameter of approximately 10 mm was obtained by rotation from both sides. A capsule agent was obtained by charging the above-mentioned content in the film at a ratio of the content to the film of 40:60. As a result that the same test as in Example 3 concerning the content of the capsule agent was carried out, the color tone, the odor and the antibacterial action, and further its storage stability were good. Further, the test of the storage stability was carried out by sealing up the capsule obtained in a case made of a PE material.

Example 21

A liquid bactericide for a wet tissue was obtained according to the compounding components shown in the following Table 20.

TABLE 20

| Compound component | Compounding amount (weight %) |
| --- | --- |
| Ethanol | 30.0 |
| Hinokitiol | 0.05 |
| Aluminum chloride hexa-hydrate | 0.735 |
| Propylene glycol | 5.0 |
| Sucrose fatty acid ester | 0.5 |
| Edetic acid salt | 0.1 |
| Deionized water | Residue |

The manufacture of the bactericide was carried out by a method of adding, mixing and dissolving other respective compounding components after dissolving hinokitiol in ethanol under room temperature (20° C.)

Then, a wet tissue for sterilization was obtained by impregnating 3 ml of the bactericide in the non-woven clothes (Bemberg) which were cut in a size of 15 cm×20 cm.

As a result of testing the wet tissue for the sterilization, no coloration just after production occurred on the non-woven fabric which is a base material, and no odor was also generated. Further, sterilization performance was also good. And, these characteristics were not changed when the wet tissue for the sterilization was stored in a state where it was sealed up in a parcel bag made of a polypropylene. The sterilization performance and storage stability were carried out by the same test method as shown in Example 3.

Example 22

A hair growth promoter was obtained according to the compounding components shown in the following Table 21.

TABLE 21

| Component partition | Compounding component | Compounding amount (weight %) |
|---|---|---|
| O | Sucrose fatty acid ester | 1.0 |
|   | Ethanol | 60.0 |
|   | Ethinylestradiol | 0.05 |
|   | Amidopropyl betaine | 1.0 |
|   | Hinokitiol | 0.1 |
|   | Perfume | 0.5 |
| P | Dipotassium glycyrrhizate | 0.1 |
|   | Japanese green gentian extract | 0.1 |
|   | Aluminum chloride hexa-hydrate salt | 1.47 |
|   | Deionized water | Residue |

The manufacture of the hair growth promoter was carried out according to the following method. Namely, respective components of the partition O and respective components of the partition P are dissolved under a temperature of 50° C. in a state of respectively mixing them. Subsequently, the solution dissolving the partition P is gradually added to the solution dissolving the partition O and mixed. Then, a hair growth promoter was obtained by cooling this mixed solution to room temperature (20° C.). 500 ml of the hair growth promoter was charged in a fixed glass vessel. The hair growth promoter assumes a light yellow color tone just after manufacture, and an odor inherent in hinokitiol did not occur. Further, sterilization performance for head hide bacteria was good, and the storage stability of these characteristics was good. Further, the sterilization performance and storage stability were carried out according to the same test method shown in Example 3. And, concerning the hair growth promoter, the following test of dandruff depression effect was carried out. That is, fifteen men who have the generation of comparatively much dandruff were divided into three groups by five men. Concerning the respective above-mentioned hair growth promoter, respective 5 ml of one just after production, one after storage and a blank in which hinokitiol in the compounding components shown in Table 21 was substituted with deionized water, were dispensed on hair after being washed with a shampoo, to the persons belonging to respective groups.

As a result that a quantity of protein contained in the waste from the head gathered after this dispensation was compared with that gathered before dispensation, one just after production and one after storage among the above-mentioned hair growth promoters deteriorated the content of a quantity of protein by around 50% in average. Further, the quantity of the deterioration by the blank was only around 30%.

The deterioration of a quantity of generation of dandruff is identified by this.

Example 23

A powdery baby powder was obtained by the compounding components of the following Table 22.

TABLE 22

| Compounding component | Compounding amount (weight %) |
|---|---|
| Tarc | 75.0 |
| Kaolin | 5.0 |
| Sericite | 14.9 |
| Titanium dioxide | 5.0 |
| Aluminum hinokitiolate | 0.1 |

The manufacture of the baby powder was carried out according to a method that after a talc, a kaolin, a sericite and titanium dioxide were mixed and pulverized with a Henschel mixer, and further aluminum hinokitiolate (a molar ratio of 1:1) was added and furthermore pulverized, the powder was passed through a riddle of 100 mesh. 100 g of the baby powder obtained was charged in a kettle made by aluminum, and it was sealed up.

The baby powder indicated a milk-white type color just after production, an odor inherent in hinokitiol was not generated, and sterilization performance was good. Further, the storage stability of these characteristics was recognized. Further, the sterilization performance and storage stability were carried out according to the same test method shown in Example 3.

Example 24

A fluid bathing agent was obtained according to the compounding components of the following Table 23.

TABLE 23

| Compounding component | Compounding amount (weight %) |
|---|---|
| Liquid paraffin | 54.98 |
| Squalane | 10.0 |
| Hiba Oil | 20.0 |
| Sorbitan oleate | 5.0 |
| POE(5)oleyl ether | 10.0 |
| Aluminum distearate | 0.05 |

Further, a hiba oil is an essential oil containing 1% by weight of hinokitiol.

The manufacture of the bathing agent was carried out by a method that the respective compound components were mixed, homogeneously dissolved by heating at 70° C., and cooled by standing alone. 250 ml of the bathing agent obtained was charged in a white opaque bottle made of a polypropylene, and it was sealed up.

The bathing agent assumed a slight brown color just after production, and an odor inherent in hinokitiol did not occur. Further, sterilization performance was good, and the storage stability of these characteristics was recognized. Further, the sterilization performance and storage stability were carried out according to the same test method shown in Example 3.

Example 25

A fluid bactericide for dermatophytosis was obtained according to the compounding components of the following Table 24.

TABLE 24

| Component partition | Compounding component | Compounding amount (weight %) |
|---|---|---|
| Q | Hinokitiol | 0.1 |
|   | Ethanol | 50.0 |
| R | Lauryldimethylamine oxide | 3.0 |
|   | Aluminum chloride hexa-hydrate salt | 1.47 |
|   | Deionized water | Residue |

The manufacture of the bactericide for dermatophytosis was carried out according to a method that the respective components of the partition Q and components of the partition R were dissolved under room temperature, and then the dissolved liquid comprising the partition R was gradually added in the dissolved liquid comprising the partition Q to be mixed.

100 ml of the bactericide for dermatophytosis obtained was charged in a fixed vessel made of a polypropylene. The bactericide for dermatophytosis obtained assumed colorless transparency just after production, and an odor inherent in hinokitiol did not occur. Further, sterilization performance was good, and the storage stability of these characteristics was recognized. Further, the sterilization performance and storage stability were carried out according to the same test method shown in Example 3.

Example 26

A mixed-liquid type antiperspirant was obtained according to the compounding components of the following Table 25.

TABLE 25

| Component partition | Compounding component | Compounding amount (weight %) |
|---|---|---|
| S | Silicon-treated talc | 25 |
|   | Aluminum chlorohydrate | 50 |
|   | Silicic acid anhydride | 25 |
| T | Trichlosan | 1.0 |
|   | Hinokitiol | 1.0 |
|   | Isopropylmyristate | 70.0 |
|   | Dimethylpolysiloxane | 20.0 |
|   | Sorbitan fatty acid ester | 6.0 |
|   | Perfume | 2.0 |

Further, the compounding amount of the respective components was shown as the compounding rate of the respective partition.

The manufacture of the antiperspirant was carried out according to a method that the respective components of the partition S were pulverized by grinding, and then 5 parts by weight of the pulverized material was added in 5 parts by weight of the mixed solution of the respective components of the partition T and homogenized. 10 parts by weight of the antiperspirant obtained and 90 parts by weight of LP gas were charged in an aerosol vessel capable of spraying.

The antiperspirant obtained was a white opaque suspension liquid just after production, and an odor peculiar to hinokitiol did not occur. Further, the antibacterial bactericidal effect for microbe which always exists on skin concerning a spray agent from the inside of the aerosol vessel, was good and the storage stability of these characteristics was recognized. Further, the sterilization performance and storage stability were carried out according to the same test method shown in Example 3.

Examples 27 to 30

A solid type detergent was obtained by the following compounding components and production method.

First of all, 15% by weight (hereinafter, merely referred to as %) of ethanol was added to 31% of mixed fatty acids (70 parts of myristic acid, 20 parts of palmitic acid, 10 parts of stearic acid, and "parts" is "parts by weight" hereinafter, the same). This was dissolved by heating under temperature conditions of 45 and 55° C. in a reaction vessel, this was neutralized with 11.5% of 48% aqueous sodium hydroxide solution and then 15% of 70% aqueous sorbitol solution, 10% of glycerol, 3% of diglyceride and 10% of refined sugar were added. The mixture was dissolved by mixing to obtain a origianl solution of the detergent.

Subsequently, aluminum hinokitiolate (a molar ratio of 3:1) or hinokitiol was compounded at a rate shown in the following Table 26, and furthermore 100% soap glue was obtained with deionized water. The soap glue was poured into a molding frame, then cooled, caked, cut off, aged and stamped to respectively obtain solid type detergents.

Further, sample No. 38 is Comparative Example. Hinokitiol is compounded as 0.1% in an original liquid of the detergent, a soap glue was furthermore obtained as 100% with deionized water, and the solid type detergent was prepared by treating this as mentioned above.

the color tone or its change, the foaming property and the bactericidal effect of these solid type detergents as samples just after production, after the test of photostability and after testing its storage stability by a method of standing alone just after production and under a temperature of 40° C. for 30 days were respectively shown in Table 26. Further, the color tone is one obtained by observing appearance with eyes. It was represented that no change of the color tone was ○, a merely slight change recognized was Δ, and a remarkable change was x. Further, foaming property was judged based on the following standard by measuring the foaming quantity which was generated by a method that 1% aqueous solution of samples was prepared with an artificial hard water containing 70 ppm of calcium carbonate and this was stirred with a mixer at a temperature state of 40° C.

TABLE 26

| | Sample No. | | | | |
|---|---|---|---|---|---|
| | Example | | | | Comparative Example |
| Compounding component | 34 | 35 | 36 | 37 | 38 |
| Aluminum hinokitiolate (weight %) | 0.01 | 0.1 | 0.5 | 1.0 | — |
| Hinokitiol (weight %) | — | — | — | — | 0.1 |
| Property At production | | | | | |
| Color tone | Colorless | Colorless | Colorless | Colorless | Light yellow |
| Foaming property | ⊙ | ⊙ | ⊙ | ⊙ | ⊙ |
| Antibacterial action (mm) | 15 | 25 | 30 | 36 | 18 |
| Photostability | | | | | |
| Color tone variation | ○ | ○ | ○ | ○ | X |
| Foaming property | ⊙ | ⊙ | ⊙ | ⊙ | ⊙ |
| Antibacterial | 14 | 24 | 29 | 34 | 9 |

TABLE 26-continued

| Compounding component | Sample No. | | | | |
|---|---|---|---|---|---|
| | Example | | | | Comparative Example |
| | 34 | 35 | 36 | 37 | 38 |
| action (mm) High temperature stability | | | | | |
| Color tone variation | ◯ | ◯ | ◯ | ◯ | X |
| Foaming property | ⊚ | ⊚ | ⊚ | ⊚ | ⊚ |
| Antibacterial action (mm) | 14 | 25 | 28 | 35 | 9 |

Namely, when the foaming quantity was more than 2200 ml, it was extremely good (referred to as ⊚), it was good (referred to as ◯) at the time of 2000–2200 ml, it was slightly inferior (referred to as Δ) at the time of 1800–2000 ml, and it was bad (referred to as x) at the time of 1800 ml or less. Further, sterilization effect was carried out according to a paper disk method. That is, a sample is prepared as 20% solution of aqueous ethanol solution (a mixed solution of the equal amount of ethanol and deionized water), and this becomes a sample solution. Further, Staphylococcus aureus is dispersed in sterilized water so as to be $10^6$ CFU/ml, 0.5 ml of the solution is inoculated onto 5 ml of broth BA agar medium. Subsequently, the agar medium is laid on 15 ml of BA agar medium which is preliminarily solidified. Subsequently, 50 μl of the sample solution mentioned above is impregnated on the paper disk (a filter paper of 8 mmφ manufactured by Toyo Filter Paper Co., Ltd.), and this is put on the central part of multilayer medium mentioned above. This was cultured under a temperature condition of 30° C. for 24 hours, and a diameter of a checked zone which occurs on the above-mentioned paper disk surface was measured in order to determine the sterilization effect. Further, the sterilization effect is proportional to the diameter of this checked zone. And the measurement of photostability was carried out by a method of exposing a sample under an irradiation of 3000 lux of a fluorescence light for 300 hours, and the measurement of high temperature stability was carried out by a method of letting a sample stand alone under a temperature of 40° C. for 30 days. The change of color tone, the foaming property and the bactericidal effect afterward were respectively tested and shown in Table 26.

It is grasped from the results of Table 26 that the detergent composition of samples No. 34 to 37 of the present invention being colorless and transparent, excellent in washing property owing to its good foaming property, and having high sterilization effect is obtained, and further these properties can be stably retained in a state of photo irradiation under severe condition and a high temperature. Further, it can be recognized that the stability is extremely improved as compared with that of Comparative Example of the sample No. 38.

Examples 31 to 35

A liquid body shampoo was obtained according to the following compounding components and production method.

First of all, 10% of potassium laurate, 5% of potassium myristate, 5% of glycerol, 10% of 1,3-butylene glycol and 10% of deionized water were mixed. The mixture was dissolved by heating under a temperature condition of 75° C., and 20% of 2% aqueous methyl cellulose solution was added to the dissolved mixture and dissolved by mixing to obtain an original liquid of a detergent.

Subsequently, hinokitiol and aluminum chloride hexahydrate salt were mixed in aqueous ethanol solution at a molar ratio and the compounding amount shown in the following Table 27, and the complex compound of hinokitiol with an aluminum compound was respectively formed in the solution.

Then, 2% of the solution containing these complex compounds was respectively compounded in the abovementioned original liquid of the detergent, and 100% was made with deionized water to respectively obtain the liquid detergents. Further, 300 ml of these liquid detergents were respectively charged in a colorless and transparent bottle made of polyvinyl chloride.

TABLE 27

| | Sample No. Compounding amount (weight %) | | | | | | |
|---|---|---|---|---|---|---|---|
| | Comparative Example | | Example | | | | |
| Compounding component | 39 | 40 | 41 | 42 | 43 | 44 | 45 |
| Hinokitiol | 5 | 5 | 5 | 5 | 5 | 5 | 5 |
| Aluminum chloride hexa-hydrate salt | 0.074 | 0.222 | 0.370 | 1.481 | 3.705 | 7.406 | 14.81 |
| Hinokitiol/Aluminum chloride hexa-hydrate salt (molar ratio) | 100/1 | 100/3 | 100/5 | 100/20 | 100/50 | 100/100 | 100/200 |
| Ethanol | 60 | 60 | 60 | 60 | 60 | 60 | 60 |
| Deionized water | Residue | Residue | Residue | Residue | Residue | Residue | Residue |
| Property | | | | | | | |
| At production | | | | | | | |
| Color tone | Yellow | Red | Light yellow | Light yellow | Colorless | Colorless | Colorless |
| Foaming property | ⊚ | ⊚ | ⊚ | ⊚ | ⊚ | ⊚ | ◯ |
| Antibacterial action (mm) | 19 | 20 | 20 | 20 | 20 | 22 | 24 |
| Photostability | | | | | | | |
| Color tone variation | X | Δ | ◯ | ◯ | ◯ | ◯ | ◯ |

TABLE 27-continued

|  | Sample No. Compounding amount (weight %) | | | | | | |
|---|---|---|---|---|---|---|---|
|  | Comparative Example | | Example | | | | |
| Compounding component | 39 | 40 | 41 | 42 | 43 | 44 | 45 |
| Foaming property | ◉ | ◉ | ◉ | ◉ | ◉ | ◉ | ○ |
| Antibacterial action (mm) | 10 | 12 | 19 | 19 | 19 | 21 | 23 |
| High temperature stability |  |  |  |  |  |  |  |
| Color tone variation | ○ | ○ | ○ | ○ | ○ | ○ | ○ |
| Foaming property | ◉ | ◉ | ◉ | ◉ | ◉ | ◉ | ○ |
| Antibacterial action (mm) | 19 | 20 | 20 | 20 | 20 | 22 | 24 |
| Coloration state of vessel body | X | Δ | ○ | ○ | ○ | ○ | ○ |

Concerning the prepared solution of the above-mentioned complex compound, the solution having a molar ratio of hinokitiol and aluminum chloride hexa-hydrate salt of 100:1 was Comparative Example 2, and one having a ratio of 100:3 was Comparative Example 3.

The color tone or its change, the foaming property and the bactericidal effect of these liquid type detergents as samples at the time of production, after the test of photostability and after testing high temperature stability were tested according to the same manner as in the above-mentioned Examples 27 to 30, and the results were respectively shown.

Further, the coloration state of the bottle container body is one obtained by observing appearance with eyes, after said detergent composition was charged in a container made of a resin and this stood alone under a high temperature condition for 30 days. It was represented that no change of the color tone was ○, a merely slight change recognized was Δ, and a remarkable change was x.

It is grasped from the results of Table 27 that when the complex compound to be compounded has 5 mole or more of the aluminum compound per 100 mole of hinokitiol, the detergent composition excellent in washing property owing to its good foaming property and having high sterilization effect is obtained in like manner as in the present Examples shown in samples No. 41 to 45, and further these properties can be stably retained in a state of photo irradiation under severe condition and a high temperature. Further, it can be recognized from the results of Examples 43 to 45 that when a compounding molar ratio of the aluminum compound exceeds 50 mole, a colorless and transparent one is obtained and no color change of the bottle body (container) occurs.

Further, it can be recognized from the results of Comparative Examples of samples No. 39 and 40 that when a compounding molar ratio of the aluminum compound is less than 5 mole, said detergent composition assumes a deep color tone and further the change of color tone occurs particularly under a condition of photo irradiation. Therefore, this composition gives a low grade one. Further, the bottle body is transparent but became yellow.

Examples 36 to 39

A creamy detergent was obtained according to the following compounding components and production method.

First of all, 10% of 30% coconut oil fatty acid acylmethyl taurine, 25% of mono sodium N-lauroylacylglutamate, 10% of a polyethylene glycol (1500), 5% of a polyethylene glycl (20000), 10% of glycerol and 20% of deionized water were mixed. Hinokitiol was mixed and dissolved in the mixture dissolved by heating at 75° C. so as to be 0.1 Then, the aluminum compounds were respectively mixed with the mixed solution at a rate shown in the following Table 28, and it was made 100% with deionized water. Subsequently, the respective creamy detergents were obtained by cooling them to 30° C. with a heat exchanger. And 60 g of them was respectively charged in a tube type container made of an opaque polyethylene.

The change of color tone, the foaming property and the bactericidal effect of the detergents and the coloration state of the container body were tested according to the same manner as described above.

It is grasped from the results of Table 28 that one being colorless is respectively obtained form any of the detergent compositions of the present Examples of samples No. 46 to 49, a desired foaming property and sterilization effect are stably retained, and further discoloration action to the container body does not occur. Further, it is assumed from this that hinokitiol forms complex compounds with various kind of aluminum compounds in the above-mentioned mixed solution.

TABLE 28

|  | Sample No. | | | | |
|---|---|---|---|---|---|
|  | Example | | | | Comparative Example |
| Compounding component | 46 | 47 | 48 | 49 | 50 |
| Hinokitiol | 0.1 | 0.1 | 0.1 | 0.1 | 0.1 |
| Aluminum tristearate | 0.5 | — | — | — | — |
| Aluminum lactate | — | 1.0 | — | — | — |
| Aluminum hydroxide | — | — | 2.0 | — | — |
| Aluminum oxide | — | — | — | 3.0 | — |
| Property |  |  |  |  |  |
| At production |  |  |  |  |  |
| Color tone | Colorless | Colorless | Colorless | Colorless | Red brown |
| Foaming property | ◉ | ◉ | ○ | ○ | ○ |
| Antibacterial action (mm) | 21 | 20 | 21 | 21 | 18 |
| High temperature stability |  |  |  |  |  |
| Color tone variation | ○ | ○ | ○ | ○ | ○ |
| Foaming property | ◉ | ◉ | ○ | ○ | ○ |

TABLE 28-continued

| | Sample No. | | | | |
|---|---|---|---|---|---|
| Compounding | Example | | | | Comparative Example |
| component | 46 | 47 | 48 | 49 | 50 |
| Antibacterial action (mm) | 21 | 20 | 20 | 20 | 17 |
| Coloration state of vessel body | ○ | ○ | ○ | ○ | X |

Example 40

A shampoo liquid was obtained according to the following compounding components and production method.

First of all, 20% of a taurine solution of 30% coconut oil fatty acid acylmethyl and 20% of a lysine solution of 30% coconut oil fatty acid were dissolved. A solution dissolving 0.2% of a cationic cellulose in 20% of deionized water was added to the dissolved solution and a residual part of deionized water was further added. The mixture was heated to 60° C. and 0.1% of an edetic acid salt was added and dissolved. Subsequently, 2.0% of ethylene glycol distearate and 0.2% of citric acid were added to this, and 0.1% of aluminum hinokitiolate was further added and mixed to be dissolved. A cream-white shampoo liquid was obtained by cooling the mixture to 30° C. with a heat exchanger. And 550 ml of the shampoo liquid was charged in a transparent bottle made of a polyethylene.

The coloration change of the shampoo liquid obtained could not be observed at all in a state in which the liquid was charged in the bottle after the test of photo stability and high temperature stability in the same manner as described above, and the shampoo liquid had a good foaming property and kept a bactericidal effect of 20 mm or more in the fore-mentioned paper disk method before and after the time of the test and did not discolor the bottle itself.

Example 40

A liquid hand soap for medical use was obtained according to the following compounding components and production method.

First of all, 10% of triethanolamine laurate, 5% of diethanolamide of coconut oil fatty acid, 0.1% of an edetic acid salt, 10% of deionized water were mixed and dissolved by heating at 70° C. 0.15% of aluminum chloride hexa-hydrate salt, 0.05% of hinokitiol and the residual part of deionized water were added to this and mixed to be dissolved. The mixture was cooled to 25° C. with a heat exchanger to obtain a transparent liquid detergent. 400 ml of the liquid detergent was charged in a transparent bottle made of a polyethylene equipped with a dispenser.

The coloration change of the liquid detergent obtained could not be observed at all in a state in which the liquid was charged in the bottle after the test of photo stability and high temperature stability in the same manner as described above, and the liquid detergent had a good foaming property and kept a bactericidal effect of 20 mm or more in the fore-mentioned paper disk method before and after the time of the test and did not discolor the bottle itself.

Example 41

A liquid rinse was obtained according to the following compounding components and production method.

First of all, 1.0% of dipropylene glycol, 2.6% of cetyl alcohol, 2.0% of stearyl trimethylammonium chloride, 0.1% of citric acid and 50% of deionized water were mixed and dissolved by heating at 70° C. A mixture dissolving 0.05% of aluminum hinokitiolate and 3.0% of liquid paraffin (70) was added to this and emulsified with a homo-mixer, and then further 0.3% of a perfume and the residual part of deionized water were added and mixed to be dissolved. The mixture was cooled to 30° C. with a heat exchanger to obtain a milk-white rinse. 400 ml of the rinse was charged in a transparent bottle made of a polyethylene.

The coloration change of the rinse obtained just after production could not be observed at all in a state in which the liquid was charged in the bottle after the test of photo stability and high temperature stability in the same manner as described above, and the rinse had a good foaming property and kept a bactericidal effect of 20 mm or more in the fore-mentioned paper disk method before and after the time of the test and did not discolor the bottle itself.

Example 42

A granular detergent was obtained according to the following compounding components and production method.

First of all, 47.0% of mono potassium N-lauroylacylglutamate, 10.0% of potassium laurate, 30.0% of lactic acid, 9.9% of a polyethylene powder, 4.5% of ethyl cellulose and 0.1% of aluminum hinokitiolate were mixed and homogeneously pulverized by mixing with a Henschel mixer. Then, 20 part of ethanol was added to 100 part of the pulverized product to obtain a kneaded product. The kneaded product was extruded through a screen of 32 mesh with a extruding granulater to obtain a columnar kneaded product. After this was air-dried under room temperature (25° C.) for 64 hours, it was extruded through a screen of 35 mesh to obtain a granular product. This was further sieved to one which passed through 32 mesh but did not passed through 60 mesh to obtain a granular detergent. Further, the granular detergent was packed to 3 g of respective aluminum pouches.

The granular detergent assumed a white appearence just after production, and the change of its color tone in a state of the packs was not recognized at all just after the test of photo stability and high temperature stability in the same manner as described above. Further, it was recognized that it had a good foaming property and kept a bactericidal effect of 20 mm or more before and after the time of the test.

Example 43

A latex detergent for a tableware and the like was obtained according to the following compounding components and production method.

First of all, 5% of sucrose fatty acid ester, 2% of glycerol, 0.1% of a xanthane gum, 0.1% of hinokitiol, 0.5% of aluminum distearate and 92.3% of an olive oil were mixed under a condition of a temperature of 70° C. to obtain a mixed solution. Then, the mixed solution was cooled to 35° C. while standing alone to obtain a latex detergent for a tableware and the like. 500 ml of the detergent was charged in a fixed bottle made of a polyethylene.

The detergent for a tableware and the like assumed a white opaque latex just after production, and did not generate an odor inherent in hinokitiol. Further, the change of its color tone in a state where it was charged in the above-mentioned bottle was not recognized at all just after the test of photo stability and high temperature stability in the same manner as described above. Further, it was recognized that it had a good foaming property and kept a bactericidal effect of 20 mm or more before and after the time of the test. Further, the detergent can be used for tablewares and the like and production machines in addition to the tableware and the like.

Example 44

A detergent for clothes was obtained according to the compounding components shown in the following Table 29.

TABLE 29

| Compounding component | Compounding amount (weight %) |
| --- | --- |
| Sodium laurylsulfate | 10.0 |
| Diethanolamide of coconut oil fatty acid | 3.0 |
| Ammonium xylenesulfonate | 5.0 |
| Hinokitiol | 0.1 |
| Ethanol | 2.0 |
| Aluminum chloride hexa-hydrate salt | 0.2 |
| Deionized Water | 79.7 |

The manufacture of the detergent for clothes was carried out as follows.

First of all, sodium laurylsulfate, diethanolamide of coconut fatty acid, ammonium xylenesulfonate and 69.7% by weight of deionized water were mixed and dissolved under room temperature. Hinokitiol was dissolved in ethanol under room temperature, and one dissolving aluminum chloride hexa-hydrate salt in 10% amount of deionized water was added to this to prepare a solution of hinokitiol aluminum. The solution of aluminum hinokitiolate was added to the above-mentioned dissolved solution by mixing, and dissolved by mixing to obtain a detergent for clothes. Further, 500 ml of the detergent was charged in a white opaque bottle made of a polypropylene.

The detergent for clothes assumed a colorless transparent appearance just after production, did not generate an odor inherent in hinokitiol, and a bactericidal effect was good. Further, the change of these properties in a state where it was charged in the above-mentioned bottle was not recognized at all just after the test of photo stability and high temperature stability in the same manner as described above, and it was recognized to have a good foaming property before and after the time of the test. Further, the bactericidal effect of the detergent presents an action for preventing or reducing the occurrence of allergic symptoms as for clothes of an allergy patient.

Example 45

A dentifrice was obtained according to the compounding components shown in the following Table 30.

TABLE 30

| Compounding component | Compounding amount (weight %) |
| --- | --- |
| Silicic anhydride | 15.0 |
| Glycerol | 5.0 |
| Sorbit | 5.0 |
| Carboxymethyl cellulose | 1.5 |
| Sodium saccharate | 0.05 |
| Hinokitiol | 0.1 |
| Aluminum hydroxide | 35.0 |
| Sodium laurylsulfate | 2.0 |

TABLE 30-continued

| Compounding component | Compounding amount (weight %) |
| --- | --- |
| Perfume | 1.0 |
| Deionized water | Residue |

The manufacture of the detergent for clothes was carried out as follows.

First of all, carboxymethyl cellulose, glycerol and sorbitol were mixed in deionized water under normal temperature. Silicic anhydride, aluminum hydroxide, sodium laurylsulfate, hinokitiol, sodium saccharate and perfume were added and dissolved by mixing. Then, this was degassed under reduced pressure to obtain a paste dentifrice. Further, 300 ml of the dentifrice was charged in a fixed tube container made of a laminate material of a polyethylene and the like.

The dentifrice assumed a white opaque appearance just after production and did not generate an odor inherent in hinokitiol, and a bactericidal effect was good. Further, the change of these properties was not recognized at all just after the test of photo stability and high temperature stability in the same manner as described above. Further, a good cleansing effect for mouth was obtained before and after the time of the test.

EFFECT OF THE INVENTION

According to the present invention, as hinokitiol being an effective component is kept in a stable state against optical irradiation, heat and the like from the outside and in a chemically and successively stable state, antibacterial, bactericidal and antiseptic effects which hinokitiol has can be effectively exhibited for a long term.

Further, various kind of useful dermatologic agents and detergent compositions can be obtained because of the above-mentioned effects without causing the deterioration of usability and quality, and do not cause the degeneration of discoloration and the like for the containers even when these containers are formed by a plastic material.

We claim:

1. An antibacterial, bactericidal and antiseptic agent comprising an aluminum salt of hinokitiol or a complex compound of hinokitiol with an aluminum compound.

2. An antibacterial, bactericidal and antiseptic agent according to claim 1 wherein the above-mentioned aluminum compound comprises one or more selected from the group consisting of aluminum oxide, aluminum hydroxide and its salt or a complex compound, aluminic acid and its salt or a complex compound, an aluminum salt with an inorganic acidic compound or its complex compound, and an aluminum salt of an organic acidic compound or its complex compound.

3. An antibacterial, bactericidal and antiseptic agent according to claim 1 or claim 2 wherein the above-mentioned aluminum salt of an organic acidic compound is one or more selected from the group consisting of an aluminum salt of a mono basic or dibasic carboxylic acid, an aluminum salt of a fatty acid, an aluminum salt of a amino acid, an aluminum salt of an anionic surface active agent, and a substitution product with aluminum of an organic polymer compound.

4. An antibacterial, bactericidal and antiseptic agent according to claim 1 or claim 2 wherein a complex compound of hinokitiol with an aluminum compound is prepared at a molar ratio of 5 mole or more per 100 mole of hinokitiol.

5. A dermatologic preparation containing an antibacterial, bactericidal and antiseptic agent according to claim 1 or claim 2 in an effective antibacterial, bactericidal and antiseptic amount.

6. A dermatologic preparation according to claim 5 wherein an aluminum salt of hinokitiol or/and a complex compound of hinokitiol with an aluminum compound is contained in an amount of from 0.01 to 5% by weight as an amount of hinokitiol.

7. A detergent composition containing an antibacterial, bactericidal and antiseptic agent according to claim 1 or claim 2 in an effective antibacterial, bactericidal and antiseptic amount.

8. A detergent composition according to claim 7 wherein an aluminum salt of hinokitiol or/and a complex compound of hinokitiol with an aluminum compound is contained in an amount of from 0.001 to 10% by weight as an amount of hinokitiol.

\* \* \* \* \*